(12) United States Patent
Keil (10) Patent No.: US 10,467,377 B2
(45) Date of Patent: Nov. 5, 2019

(54) METHOD AND MEDICAL IMAGING APPARATUS FOR GENERATING A FAVORITES SET OF PROTOCOLS FOR CONTROLLING THE MEDICAL IMAGING APPARATUS

(71) Applicant: Siemens Healthcare GmbH, Erlangen (DE)

(72) Inventor: Miriam Keil, Erlangen-Dechsendorf (DE)

(73) Assignee: Siemens Healthcare GmbH, Erlangen (DE)

(*) Notice: Subject to any disclaimer, the term of this patent is extended or adjusted under 35 U.S.C. 154(b) by 105 days.

(21) Appl. No.: 15/685,297

(22) Filed: Aug. 24, 2017

(65) Prior Publication Data
US 2018/0060486 A1  Mar. 1, 2018

(30) Foreign Application Priority Data
Aug. 25, 2016 (EP) .................. 16185605

(51) Int. Cl.
| | |
|---|---|
| *G06F 19/00* | (2018.01) |
| *G06F 3/0484* | (2013.01) |
| *G16H 40/63* | (2018.01) |
| *G06Q 50/22* | (2018.01) |
| *G06T 7/70* | (2017.01) |
| *H04L 29/06* | (2006.01) |
| *G06T 7/00* | (2017.01) |

(52) U.S. Cl.
CPC ............ *G06F 19/32* (2013.01); *G06F 3/0484* (2013.01); *G06T 7/70* (2017.01); *G16H 40/63* (2018.01); *H04L 29/06* (2013.01); *G06Q 50/22* (2013.01); *G06T 7/0012* (2013.01)

(58) Field of Classification Search
CPC ....................................................... G06F 19/00
USPC ........................................ 715/763, 748, 717
See application file for complete search history.

(56) References Cited

U.S. PATENT DOCUMENTS

| | | | |
|---|---|---|---|
| 2004/0082845 A1* | 4/2004 | Matsumoto | A61B 6/00 600/407 |
| 2005/0267348 A1 | 12/2005 | Wollenweber et al. | |
| 2013/0012835 A1* | 1/2013 | Chono | A61B 8/463 600/587 |
| 2016/0092634 A1* | 3/2016 | Kroell | G06F 19/321 705/2 |
| 2017/0196531 A1* | 7/2017 | Bae | A61B 6/4441 |
| 2017/0221234 A1* | 8/2017 | Chen | G06T 11/008 |

* cited by examiner

*Primary Examiner* — Cao H Nguyen
(74) *Attorney, Agent, or Firm* — Schiff Hardin LLP (57) ABSTRACT

In a method and apparatus for generating a favorites set containing a number of protocols, each protocol of the multiple protocols including control parameters for controlling a medical imaging apparatus, a computer determines a system parameter of the medical imaging apparatus, and an entry is made into the computer that designates a requirement of a user of the medical imaging apparatus. The computer then automatically defines a favorites set, taking into account the system parameter and the requirement.

19 Claims, 2 Drawing Sheets

METHOD AND MEDICAL IMAGING APPARATUS FOR GENERATING A FAVORITES SET OF PROTOCOLS FOR CONTROLLING THE MEDICAL IMAGING APPARATUS

BACKGROUND OF THE INVENTION

Field of the Invention

The invention concerns a method, a medical imaging apparatus and a non-transitory computer-readable data storage medium for generating a favorites set of multiple protocols, each protocol of the multiple protocols containing control parameters for controlling the medical imaging apparatus.

Description of the Prior Art

Medical imaging apparatuses usually have a number of components, control of which is typically executed by software that causes algorithms to be executed. Medical imaging apparatuses thus can generate image data of patients or other examination objects. Based on the image data, clinical diagnoses can be created and diseases can be diagnosed. Depending on the clinical objective, the type of medical imaging apparatus to be used, and typically control parameters for controlling the medical imaging apparatus, can be chosen. These control parameters, of which there is usually a large number, are typically referred to collectively as a protocol. For the examination of a patient, it may be necessary for the medical imaging apparatus to be controlled by a number of individually distinct protocols.

For controlling a medical imaging apparatus, typically one protocol can be selected among a number of protocols, and optionally customized to the examination to be executed or to the patient. The number of protocols available for selection will typically depend on the medical imaging apparatus and/or on a component of the medical imaging apparatus and/or the installed software. In addition, preferences of a user of the medical imaging apparatus can be taken into account in the protocols available for selection. The number of protocols available for selection can be referred to as a favorites set.

Such a favorites set is typically defined during installation of the medical imaging apparatus. If a component of the medical imaging apparatus is changed and/or if different software is installed, adaptation of the favorites set may be required and/or advantageous. The definition and/or the adaptation of the favorites set is typically executed by a trained specialist.

SUMMARY OF THE INVENTION

An object of the invention is to provide a method for generating a favorites set containing multiple protocols for controlling a medical imaging apparatus, which enables a particularly customized and easy generation of the favorites set in accordance with the needs of a user of the medical imaging apparatus.

The method according to the invention for generating a favorites set containing a number of protocols, each protocol of the multiple protocols including control parameters for controlling a medical imaging apparatus, has the following method steps. In a computer, determining a system parameter of the medical imaging apparatus, and an entry is made into the computer that designates a requirement of a user of the medical imaging apparatus. The computer then automatically defines a favorites set, taking into account the system parameter and the requirement.

In medical imaging, image data are created that depict the anatomy or internal structure of an examination object in the form of sectional images or projections. An examination object can be a patient, a training person or a phantom. A medical imaging apparatus is a system to execute medical imaging procedures. Examples of medical imaging apparatuses are X-ray apparatuses, ultrasound devices, computed tomography systems and magnetic resonance systems.

To use a medical imaging apparatus for medical imaging, the medical imaging apparatus and/or components of the medical imaging apparatus are controlled by different control parameters that are chosen depending on the medical imaging apparatus. The control parameters that are chosen may depend on the medical imaging apparatus, on the examination object and/or on the clinical objective. Control parameters can be physical variables such as a voltage to be applied to a component, for example, to a radio-frequency coil or to an X-ray tube. If the medical imaging apparatus is a magnetic resonance apparatus, then a control parameter can be a length of time between two radio-frequency pulses and/or magnetic field gradients to be played out. Control parameters can characterize the image data to be recorded by specifying, for example, a resolution.

Typically, control parameters are chosen depending on the examination object and/or a clinical objective, in particular depending on the reason for the examination by operation of the medical imaging apparatus.

A set of control parameters, based on which set the medical imaging apparatus can be controlled and image data can be generated, is referred to as a protocol. The image data generated with the control parameters of a protocol preferably have a uniform contrast and preferably represent a sub-area of the examination object. Particularly in the case of examinations with magnetic resonance systems, a sub-area of the examination object is represented in an examination in at least one further contrast. A further protocol containing other control parameters can be used for this purpose. For an examination of an examination object, the control of the medical imaging apparatus can thus be effected by a number of protocols.

When the medical imaging apparatus is being controlled, the control parameters are forwarded to a control computer of the medical imaging apparatus, and this control computer controls at least one component in accordance with the control parameters. If a control parameter is not a physical variable, the control computer can translate the control parameter into at least one physical variable.

The method according to the invention is typically not executed for a specific examination object. The method according to the invention is typically executed without a patient being examined and/or without a patient being positioned such that an examination could be executed with the medical imaging apparatus. During execution of the method according to the invention, typically no controlling of the medical imaging apparatus occurs. In particular, during execution of the method according to the invention typically no image data from a patient are generated within the scope of a clinical examination.

First, at least one system parameter of the medical imaging apparatus is determined. The system parameter preferably characterizes at least one characteristic of the medical imaging system. The system parameter may be, for example, information relating to a component which of medical imaging apparatus. For example, an option and/or a limitation for a control parameter, and consequently for a protocol, may be extracted from a system parameter. The at least one system parameter of the medical imaging apparatus is preferably determined automatically by an algorithm.

A user of the medical imaging apparatus is typically a person who monitors the medical imaging apparatus during medical imaging and/or selects the protocols for an examination of a patient. A user can be a radiologist who analyzes the image data generated with the medical imaging apparatus. A user can be an engineer who checks the functionality of the medical imaging apparatus upon the installation thereof and matches this to the needs of a person who is to operate the medical imaging apparatus.

The user specifies a requirement, this requirement preferably relating to the recording of medical image data. Preferably at least one protocol is generated which takes into account and/or preferably complies with the requirement. The user can specify two or more requirements, which are preferably taken into account in the generation of at least one protocol of the favorites set. When specifying at least two requirements, the user can preferably prioritize the requirements. The prioritization of the requirements is preferably taken into account when defining a favorites set. When the medical imaging apparatus is controlled in accordance with this protocol, then the requirements are typically complied with when the image data are recorded. A requirement can also relate to the image data, for example the resolution of the image data. The requirement is preferably not matched to an individual examination object or specifically to a patient. The requirement preferably specifies a general characteristic for an examination. The requirement preferably specifies a general guideline for each measurement by the medical imaging apparatus to which this requirement is to apply.

Based on the determined at least one system parameter, and the specified at least one requirement, a favorites set is determined. Preferably, a number of requirements of the user are specified, which relate to a number of protocols. The favorites set includes a number of protocols, such that all the requirements specified by the user can be fulfilled. The protocols of the favorites set are preferably usable for a number of individually distinct clinical objectives and/or examinations. The protocols of the favorites set are preferably available for all measurements by the medical imaging apparatus and can be selected by a user of the medical imaging apparatus for a specific examination. For an examination, the user can select protocols from the favorites set depending on the examination object and/or the clinical objective. The protocols contained in the favorites set will preferably meet the requirements of the user, such that preferably little or no adaptation of the protocols from the favorites set to the actual examination situation is required.

An advantage of the method according to the invention is that the favorites set contains protocols that meet the requirements of the user. When using the medical imaging apparatus, the user can access protocols from the favorites set, the favorites set having been organized in accordance with the requirements of the user. In the method according to the invention, the favorites set can be adapted by the user to the custom requirements of the user by the user himself or herself making entries into the computer, or by directing another person as to the entries to be made. Such another person is another person with a skillset and knowledge comparable to the user (i.e., not a technician). The method can be executed by a user easily and/or intuitively. The degree of detail of the requirements to be taken into account can also be defined by the user.

The method according to the invention can be executed directly by a user who monitors the medical imaging apparatus during medical imaging and/or selects the protocols for an examination of a patient, for example, an assistant medical technician and/or a radiologist. To implement the method according to the invention, there is preferably no requirement for a technician, for example, to check the functionality of the medical imaging apparatus during installation and match it to the needs of a radiologist. As a result, the favorites set can be generated directly by a user who uses the magnetic resonance device daily. By specifying the desired requirements, the user who uses the magnetic resonance device daily can adapt the favorites set to his/her wishes. In this way, problems which in communication between a technician and such a user can be avoided. Moreover, the presence of a technician is not required for generating a favorites set, which can achieve time savings and/or cost savings.

The method according to the invention can be executed if a requirement of a user for the medical imaging apparatus changes, for example. This may apply if the medical imaging apparatus is being used by a new user. If the medical imaging apparatus is situated in a radiological practice, then execution of the method according to the invention can be executed when a new radiologist enters the practice. A requirement of a user for the medical imaging apparatus may change, for example, if the user has taken part in training for such a medical imaging apparatus and/or if remuneration guidelines for examinations by the medical imaging apparatus change.

The method according to the invention can be executed if a system parameter of the medical imaging apparatus changes, for example. As a result, the favorites set can also easily be updated if there are minor changes to the medical imaging apparatus, so that the favorites set can utilize the latest system parameters of the medical imaging apparatus. If the medical imaging apparatus is a magnetic resonance system, then a system parameter will change, for example, upon acquisition of a different local receiving coil. The protocols of the favorites set that are compatible with this local receiving coil can be adapted with the method according to the invention, and thus typically improved by a user who uses the magnetic resonance device daily. The favorites set in this way can be adapted to the new system parameter. Where a current favorites set, adapted to the individual wishes of the user, is available, the customized and desired protocols can be applied quickly and reliably in examinations. In this way, reproducible results and/or image data can be generated by a medical imaging apparatus and/or a consistent quality of image data can be ensured.

In an embodiment of the method, the method is executed only when the medical imaging apparatus is reconfigured. When the medical imaging apparatus is reconfigured, typically a system parameter is changed and/or the medical imaging apparatus is arranged and/or newly installed and/or put into operation by a user for the first time. The method is therefore preferably executed not when a patient is being examined, but rather when the medical imaging apparatus is being commissioned. The method is executed, for example, after installation and/or modification of the software and/or modification of a component of the medical imaging apparatus.

An advantage of this embodiment is that no technician is required in order to generate the favorites set. The user can ensure in accordance with the embodiment of the method that the favorites set generated by the user's takes the current system parameters into account. This provides improved customization of the favorites set and a cost saving. In particular when the medical imaging apparatus is reconfigured, an adaptation of the protocols to the requirements of the user is required. If this adaptation can be made by the user in the absence of a technician, then cost and/or time savings can be made upon each reconfiguration.

In another embodiment of the method, when the favorites set is defined, a subset is selected from a core set, this core set containing a number of protocols for controlling the medical imaging apparatus. The core set preferably contains protocols that are dependent on at least one requirement and/or dependent on at least one system parameter. The core set is preferably filed on a memory unit such that the core set can be made available in the execution of the method. When the method is executed, at least one protocol from the core set can be selected when defining the favorites set based on the at least one system parameter and based on the at least one requirement that has been designated. The core set can be generated, for example, by one or more specialists, in relation to various requirements. A specialist may be a person who works in the medical imaging apparatus development environment, for example. A specialist may also be a person who adapts, in particular optimizes, the application of the medical imaging apparatus, in particular as a medical practitioner and/or together with a medical practitioner. The core set may be made available for reconfiguration of the medical imaging apparatus, for example in a memory. The memory may be a component of the medical imaging apparatus.

An advantage of this embodiment is that protocols can be made available with the core set that, for example, have been developed and/or tested by a specialist in advance. A defined quality can therefore be guaranteed for the protocols in the core set. When the favorites set is generated, if protocols from the core set are selected that fulfill the at least one given requirement and/or the at least one system parameter, then simultaneously customization can be achieved and a defined quality of the protocols can be guaranteed. No knowledge about development of a protocol is required in order to generate the favorites set in accordance with desired requirements. The user thus can select protocols according to his/her requirements and generate a favorites set even with little or no knowledge about how the medical imaging apparatus functions.

In an embodiment of the method, the system parameter is one or more of the following parameters:
  a software version of the medical imaging apparatus,
  the presence of a specific component of the medical imaging apparatus, and a particular embodiment (model or version) of a specific component of the medical imaging apparatus.

The software version can be a version of software suitable for controlling the medical imaging apparatus and/or for evaluating the data recorded with the medical imaging apparatus and/or for generating the image data. To use the software version and/or a part of the software version, the acquisition of a license for the software version may be required. The system parameter may also be the existence of a license for the software version. A medical imaging apparatus typically has a number of components that are required for generating image data. Depending on the type of medical imaging apparatus, this may be, for example, an X-ray detector, an ultrasound probe or a coil for transmitting and/or receiving electromagnetic waves. A computer may also be such a component of the medical imaging apparatus. The specific component relates preferably to the executability of at least one protocol in the favorites set.

Particularly in magnetic resonance apparatuses, the transmitting and/or receiving coils of the magnetic resonance scanner represent a limitation to the executability of certain protocols. The transmitting and/or receiving coils can typically be acquired independently of the magnetic resonance apparatus. Local transmitting and/or receiving coils are often used intuitively so that introductory training by a technician typically does not occur. To exploit the functionality of a transmitting and/or receiving coil, it is advantageous to update the favorites set, in particular the protocols of the set that are designed to use this coil when controlling the magnetic resonance device.

An advantage of this embodiment of the method is that the favorites set can easily be adapted to a current version of the medical imaging apparatus. It can thereby be ensured that the user uses the current version of the medical imaging apparatus in the best possible way. The medical imaging apparatus can be designed to detect a change in a system parameter and prompt a user to execute the method according to the invention, in particular to prompt the user to adapt the favorites set in accordance with the changed system parameter. Particularly in the case of changes to the medical imaging apparatus that do not require the presence of a technician such as the purchase of a coil and/or a remotely monitored and/or remotely controlled update of the software, the favorites set can be easily adapted, after the change, to the individual needs of the user. The change to the favorites set can be executed by the user himself/herself, which provides a time and/or cost saving compared with a complex execution requiring the presence of a technician.

In an embodiment of the method, the requirement is at least one of the following characteristics:
  quality of the image data to be generated,
  maximum and/or minimum duration of a protocol,
  maximum and/or minimum duration for a set of protocols which are required for an examination of an examination object,
  an examination area,
  a clinical objective,
  need for a contrast medium,
  degree of automation,
  possibility of custom post-processing of a protocol.

The user of the medical imaging apparatus can specify preferably at least one of these characteristics as a requirement for defining a favorites set.

The quality of the image data to be generated relates to particular characteristics of the image data which can be generated by the medical imaging apparatus. The quality of the image data can be defined, for example, by resolution and/or by blurring and/or by contrast and/or by susceptibility of the image data to movements of the examination object. As used herein, the quality of the image data relates to the image data that can be generated by controlling the medical imaging apparatus in accordance with a protocol which fulfills the at least one specified requirement. This quality is preferably a characteristic that applies independently of the examination object. An advantage of this requirement is that the user can specify a minimum required quality that can be complied with for each examination object. This can ensure a defined quality standard for the image data.

A further specifiable requirement can be a maximum and/or minimum duration of a protocol, in particular the maximum and/or the minimum period required for playing out the protocol. The maximum duration can indicate an upper limit for the duration, the protocol preferably being chosen for the favorites set such that it will last for a shorter time than the indicated maximum duration. Typically the shorter the duration of a protocol, the lower will be the probability that, when the protocol is being played out (i.e.

when the medical imaging apparatus is being controlled in accordance with this protocol), artifacts will occur due to a movement of the examination object. This can increase the quality of the image data. In addition, the specification of a maximum duration of a protocol can limit the duration which is required for the examination of an examination object. This produce a time saving. The specification of a minimum duration, moreover, can increase the quality of the image data, as typically a higher quality of image data can be achieved when the duration of a measurement is longer.

Furthermore, the user can specify a maximum and/or minimum duration for a set of protocols required for an examination of an examination object. For the examination of an examination object, depending on the type of medical imaging apparatus, a number of image data sets may be required for a sub-area of the examination object. The image data sets are typically generated here through control of the medical imaging apparatus by the use of various protocols. These various protocols can be referred to as a set of protocols that are required for an examination of an examination object. If the user can specify the maximum and/or minimum duration for such a set of protocols, then the duration for a full examination of a patient can be predicted, which contributes to the reliability of the examination planning. In addition, the specification of a maximum duration can achieve a time and/or cost saving.

A further requirement can be an examination area. An examination area is typically a region of the examination object, for example a part of the body or a part of a limb, from which image data are generated in an examination by operation of the medical imaging apparatus. Examples of an examination area can be the head, abdomen, knee or hip. The examinations of different examination areas typically require different protocols. Thus, in a head examination, the size of the examination area and/or the resolution of the image data are typically different than in the case of an examination of an abdomen. These parameters in a protocol of the favorites set are taken into account.

The examination area can be specified more precisely by the designation of a clinical objective. For example, in examinations of the heart by a magnetic resonance device, different contrasts are advantageous in the case of possible ischemia, than when monitoring the function of a cardiac valve. The clinical objective can also be specified as a requirement by the user independently of the examination area.

Particularly in the case of examinations by magnetic resonance systems, computed tomography systems and/or positron emission tomography systems (PET), the administration of a contrast medium to the examination object may occur before and/or during examinations. For example, the user may specify as a requirement whether a contrast medium is to be administered to the examination object. The time of administration, for example, can also be specified. The administration of the contrast medium is typically dependent on the examination area and/or the clinical objective. The need for a contrast medium is preferably indicated depending on the examination area and/or the clinical objective. The user therefore can indicate on an individual basis in which examinations a contrast medium is to be used.

As a further requirement, the degree of automation can be specified, for example. The degree of automation relates preferably to an examination procedure in which examination image data of an examination object are generated. For example, in the case of a high degree of automation, the favorites set can be formulated such that, after positioning of the examination object in an examination, a maximum number of interactions are required between a user of the medical imaging apparatus and the medical imaging apparatus, in order to generate all the required image data of the examination object. This maximum number is preferably five interaction, more preferably there interactions. By specifying a desired degree of automation when defining the favorites set, the qualification of a user who generates image data of an examination object based on the favorites set, can be taken into account. Similarly, the possibility for custom post-processing of at least one protocol contained in the favorites set and/or the degree to which custom post-processing is possible can be specified as a requirement. Those in the favorites set preferably largely correspond to the requirements of the user. When applying a protocol in a specific examination of an examination object, it can be advantageous to adapt further control parameters to the examination object, so that the protocol used can deviate from the protocol contained in the favorites set. The possibility for custom adaptation of a protocol thus enables optimization of a protocol for a specific examination. The quality of the image data can optionally be improved as a result. In order for uniform quality to be observed in different examinations and/or where the qualification of a user is low, it can be advantageous to enable very little or no custom post-processing of the protocols in the favorites set. In this way, a minimum quality can be ensured where the qualification of a user is low. A highly qualified user can be provided with multiple degrees of freedom for generating image data, so that the quality of the image data can be optimized with regard to the examination object and/or the clinical objective. An advantage of the embodiment is that the qualification of the at least one user can be taken into account.

Further requirements deemed appropriate by those skilled in the art can be used at any time in an alternative embodiment of the invention, without departing from the scope of protection of the invention.

The aforementioned possible requirements allow various individual demands to be taken into account when generating the favorites set, with the degree of detail of the requirements being individually defined. The favorites set generated with this embodiment of the method according to the invention can be used as the basis for a measurement of an examination object by operation of the medical imaging apparatus: the favorites set contains protocols individually tailored to the user, which can easily be selected for an examination. As specified optionally for the generation of the favorites set, the user can make further changes to the protocols or, where there is a high degree of automation, can execute the examination with few interactions with the medical imaging apparatus. Overall, an examination based on the favorites set is typically less prone to error.

In an embodiment of the method, the specification of the requirement takes the form of an input request to the user. For example, an input request can be a display on a monitor that asks the user a question and/or provides multiple options from which to select. The user can answer the question and/or select an option. This option can be a first requirement for the favorites set and/or induce a further input request, which further input request may ask for a further requirement to be designated, or the further requirement may ask to specify the first requirement more precisely. Such an embodiment of the method is particularly easy for the user to understand and intuitive to use. In this way, the user can be guided such that all the relevant requirements for the favorites set can be acquired via a number of input requests. In accordance with this embodiment, the requirements of the user can be processed unambiguously.

In another embodiment of the method, a number of requirements can be specified iteratively, a first of the number of requirements being specified more precisely by a second of the number of requirements. In this embodiment, the user can set different requirements for the favorites set, a first requirement having a first level of detail and a second requirement having a second level of detail. A requirement with the first level of detail can be specified more precisely by a requirement with the second level of detail. After the first and/or the second requirement, the user preferably defines whether he/she would like to define the requirement in more detail by yet a further requirement, for example with a third level of detail, or would like to select a further requirement of the first and/or second level of detail. The method is designed such that the specification of the requirements of the different degrees of detail is intuitively possible and follows, for example, a commonplace tree structure. According to this embodiment, it can be ensured that all requirements of interest to the user can be specified and/or the level of detail can be individually organized by the user, optionally depending on the first requirement. This enables a very flexible specification of different requirements and/or a high degree of customization.

In another embodiment of the method, if at least one requirement is not fulfilled when the favorites set is defined, a protocol that largely fulfills the at least one requirement is proposed to the user for selection.

The favorites set is defined taking into account the at least one system parameter and the at least one user requirement. The protocols in the favorites set thus are preferably compatible with the at least one system parameter and preferably fulfill all the specified requirements. Depending on the choice of the at least one requirement and/or the system parameter, however, contradictions may occur, such that no protocol is available and/or can be generated that can be played out so as to fulfill the at least one specified requirement, in particular all the specified requirements. In this case, a protocol that substantially fulfills the requirement can be generated and/or selected. A requirement is substantially fulfilled if the deviation of the protocol from the requirement is minimal.

Where two or more requirements have been specified, then a deviation can be substantially fulfilled if the totality of deviations of the protocol from the requirements is. Particularly where there are two opposing requirements, such as a high resolution and a low measurement duration, a protocol typically cannot fulfill both requirements simultaneously. The requirements can be prioritized and/or weighted by the user when they are specified, and this can be taken into account when generating the favorites set. The prioritization and/or weighting can be taken into account when a protocol is proposed for selection that substantially fulfils the at least one requirement.

The protocol that substantially fulfils the at least one requirement can be proposed to the user. The user is preferably shown the deviation compared with his/her requirement and/or given the option of selecting this protocol and/or changing at least one requirement. The advantage of this embodiment is that the user is informed if his/her requirement is not fulfilled and a best possible solution is proposed to the user.

In another embodiment of the method, the protocols of the favorites set are classified such that the protocols required for an examination of an examination object have an identical classification. The classification of the protocols can be executed by the user. The classification of the protocols also can be executed by a specialist. In the classification, at least one class is assigned to at least one protocol of the favorites set. A class can indicate, for example, an examination region and/or a clinical objective. A class preferably characterizes an examination in which the protocol is used. Multiple classes can be assigned to one protocol.

Where the medical imaging apparatus is a magnetic resonance apparatus, then if the magnetic resonance apparatus is controlled with a first protocol, image data can be generated, for example with a T2 contrast in a transverse orientation. If the magnetic resonance device is controlled with a second protocol, other image data can be generated, for example with a T1 contrast in a sagittal orientation. The first protocol and the second protocol are used preferably for an examination of a knee. The first protocol and the second protocol are therefore classified, for example, under the class "knee". The first protocol is used, for example, in examinations of the meniscus, the second protocol is used, for example, in examinations of the cartilage. The first protocol can therefore be classified under the class "meniscus", and the second protocol can therefore be classified under the class "cartilage".

An advantage of this method is that a classified favorites set can easily be searched. A user can intuitively select from the favorites set relevant protocols for an examination. This therefore shortens the preparation period for an examination and/or the errors which can occur in examinations.

In another embodiment of the method, a favorites profile is taken into account in defining the favorites set, and a self-learning algorithm updates the favorites profile based on the favorites set. The favorites set then can be defined based on at least one system parameter, and at least one user requirement, and one favorites profile. The favorites profile can describe information about the user and/or his/her use of the medical imaging apparatus and/or a further medical imaging apparatus. The favorites profile can describe information about a further user and/or his/her use of the medical imaging apparatus and/or a further medical imaging apparatus. The favorites profile preferably represents information about at least one requirement of at least one user. The favorites profile is preferably filed in a memory such that the core set can be made available for the execution of the method.

If the user has generated a favorites set, then the favorites profile can be updated such that information about the user and/or at least one requirement of the user and/or a system parameter is included, in particular stored, in the favorites profile. The self-learning algorithm preferably executes these steps automatically. The self-learning algorithm is preferably executed in a networked fashion in a number of medical imaging apparatuses. The self-learning algorithm is preferably designed such that, based on the favorites profile, the user requirement, and the system parameter, it generates a favorites set that corresponds even more closely to the wishes of the user.

In another embodiment of the method, a favorites profile is taken into account when defining the favorites set, a user executes a further customization of the favorites set based on the favorites set, and a self-learning algorithm updates the favorites profile based on the customized favorites set.

After the favorites set has been generated, the favorites set and/or protocols of the favorites set can be customized, for example post-processed, by the user. The protocols of the favorites set comprises can be adapted more precisely to the needs of the user during customization. During customization, at least one control parameter of the protocols is changed. Customization is typically carried out independently of an examination object. The customized favorites set is preferably taken into account by the self-learning algorithm in the updating of the favorites profile. If a further favorites set is generated taking into account the favorites profile embodying the customized favorites set, then the type and/or extent of the customization is typically known to the user and can be taken into account in the further favorites set. The further favorites set therefore preferably corresponds as precisely as possible to the requirements of the user and/or to the wishes of the user not expressed in the form of requirements.

In another embodiment of the method, the favorites profile is based on two favorites sets, a first of the two favorites sets being assigned to a first medical imaging apparatus and a second of the two favorites sets being assigned to a second medical imaging apparatus. The favorites profile therefore embodies favorites sets that have been generated by two distinct medical imaging apparatuses. The two medical imaging apparatuses are preferably medical imaging apparatuses of the same modality, for example both magnetic resonance apparatuses. The medical imaging apparatuses may alternatively have different modalities, so that certain requirements of the user, such as a maximum duration for a protocol, are applied to the different medical imaging apparatuses. The favorites profile embodies original favorites sets and/or customized favorites sets and/or system parameters and/or requirements of one or at least two users and/or information about the users. Based on one or more of these contributions to the favorites profile, the self-learning algorithm, when taking into account the favorites profile in order to generate a further favorites set, can recognize particularly well and/or take into account wishes of the user.

Furthermore, the invention concerns a medical imaging apparatus with a control computer having a definition processor. The definition processor is designed to execute the method according to the invention for generating a favorites set containing multiple protocols, each protocol of the multiple protocols containing control parameters for controlling the medical imaging apparatus.

To this end, the definition processor has an input, a core processor and an output. A core set of protocols and/or a favorites profile can be made available to the definition processor via the input. Further functions, algorithms or parameters needed in the method can be made available to the definition processor via the input. The favorites set and/or further results of embodiments of the method according to the invention can be made available via the output. The definition processor can be integrated in the medical imaging apparatus. The definition processor can also be installed separately from the medical imaging apparatus. The definition processor can be connected to the medical imaging apparatus.

Embodiments of the medical imaging apparatus according to the invention are analogous to the embodiments of the method according to the invention. The medical imaging apparatus can have further control components that are necessary and/or advantageous for executing the method according to the invention. The medical imaging apparatus can also be designed to transmit control signals and/or to receive and/or to process control signals in order to execute the method according to the invention. The definition processor is preferably part of the control computer of the medical imaging apparatus according to the invention. Computer programs and further software, with which the core processor of the definition processor automatically controls and/or executes the procedural sequence of the method according to the invention, can be stored on a memory of the definition processor.

The present invention also encompasses a non-transitory, computer-readable data storage medium encoded with programming instructions that, when the storage medium is loaded into a control computer or distributing computer system of a medical imaging apparatus, cause the control computer or distributed computer system to operate the medical imaging apparatus in order to implement any or all embodiments of the method according to the invention, as described above.

Examples of electronically readable data media are a DVD, a magnetic tape or a USB stick, on which electronically readable control information, in particular software, is stored.

The advantages of the medical imaging apparatus according to the invention, and the electronically readable data medium according to the invention essentially correspond to the advantages of the method according to the invention that have been described in detail above. Features, advantages and alternative embodiments mentioned above can likewise be applied to the other aspects of the invention.

DESCRIPTION OF THE PREFERRED EMBODIMENTS

Figure 1:
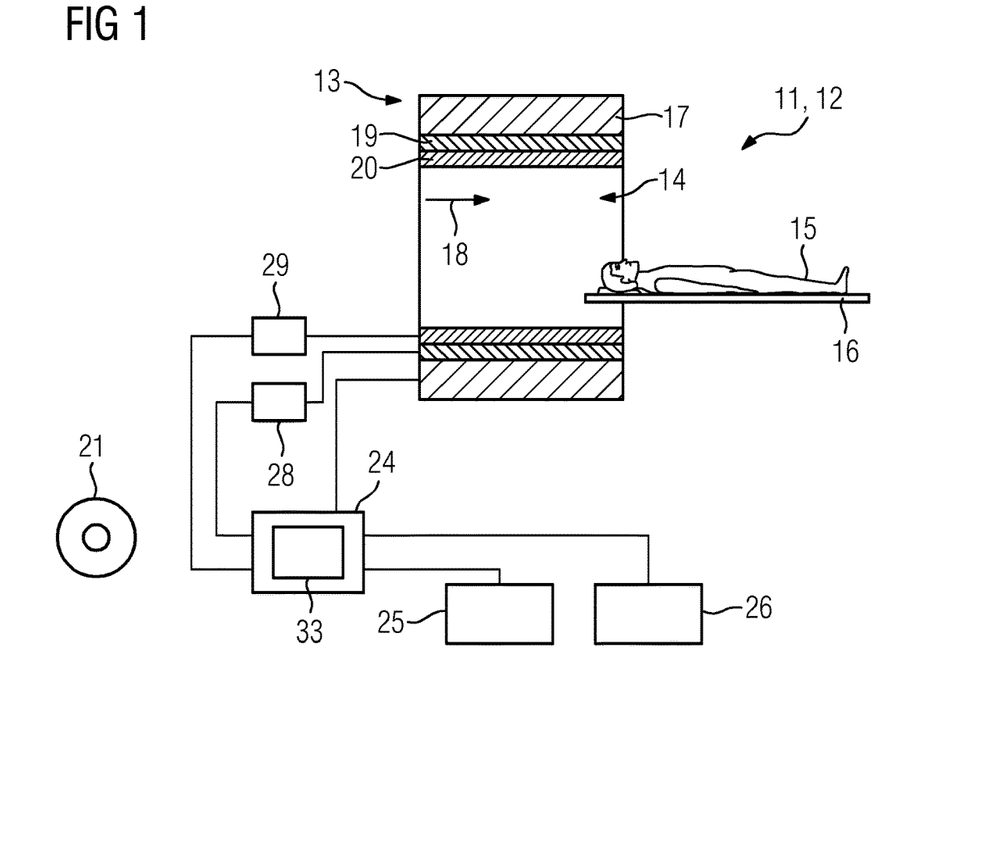
FIG. 1 is a schematic illustration of a medical imaging apparatus according to the invention.

FIG. 1 schematically shows a magnetic resonance apparatus 11 as an example of a medical imaging apparatus according to the invention for executing the method according to the invention. In principle, the design of the medical imaging apparatus is not restricted to a magnetic resonance apparatus 11, but can be other medical imaging apparatuses deemed appropriate by those skilled in the art, such as computed tomography systems, PET systems, ultrasound devices, etc.

The magnetic resonance apparatus 11 an MR data acquisition scanner 13 having a basic field magnet 17 that generates a strong and constant basic magnetic field 18. The scanner 13 has a cylindrical patient receiving area 14 for receiving a patient 15, the patient receiving area 14 being cylindrically enclosed in a circumferential direction by the scanner 13. The patient 15 can be displaced by a patient positioning device 16 of the scanner 13 into the patient receiving area 14. The patient positioning device 16 has for this purpose a patient table that is movably arranged inside the scanner 13.

The scanner 13 also has a gradient coil arrangement 19, which is used for spatially encoding MR signals during imaging. The gradient coil arrangement 19 is controlled by a gradient controller 28. Furthermore, the scanner 13 has a radio-frequency antenna 20, which in the case shown is embodied as a body coil permanently integrated in the scanner 13. The radio-frequency antenna 20 is controlled by the radio-frequency antenna controller 29 and radiates radio-frequency pulses into an examination space essentially formed by the patient receiving area 14. The radio-frequency pulses give certain nuclear spins in the examination subject 15 a magnetization that causes those nuclear spins to deviate from the field lines of the basic magnetic field 18 by an amount known as a flip angle. As these excited nuclear spins relax and return to their steady state, they emit magnetic resonance signals, which are detected by the same antenna that radiated the radio-frequency pulses, or by a different antenna.

For controlling the basic field magnet 17, the gradient controller 28 and the radio-frequency antenna controller 29, the magnetic resonance apparatus 11 has a control computer 24. The control computer 24 controls the magnetic resonance apparatus 11, for example the performance of MR control sequences, centrally. In addition, the control computer 24 has a reconstruction processor, (not shown), for reconstructing medical image data from the raw data acquired during the magnetic resonance examination. The magnetic resonance apparatus 11 has a display unit 25. Control information, such as control parameters, and reconstructed image data, can be displayed for a user on the display unit 25, for example on at least one monitor. The magnetic resonance apparatus 11 also has an input unit 26, via which information and/or imaging parameters can be entered by a user during a measuring procedure. The control computer 24 can include the gradient controller 28 and/or radio-frequency antenna controller 29 and/or the display unit 25 and/or the input unit 26.

The control computer 24 furthermore has a definition processor 33. The definition processor 33 is also designed for executing the method for generating a favorites set containing multiple protocols. For this purpose, the definition processor 33 has computer programs and/or software that can be loaded directly in a memory, (not shown) of the definition processor 33, with program code for executing the method for generating a favorites set containing multiple protocols, when the computer programs and/or software are executed in the definition processor 33. The definition processor 33 has for this purpose a core processor, (not shown), which is designed for executing the computer programs and/or software. As an alternative, the computer programs and/or software can be stored on an electronically readable data medium 21, embodied separately from the control computer 24 and/or definition processor 33.

The magnetic resonance apparatus 11 shown can have further components that magnetic resonance apparatuses usually have. The general way in which a magnetic resonance apparatus functions is known to those skilled in the art, so a detailed description of the further components is not necessary herein. The magnetic resonance apparatus 11, together with the definition processor 33, is thus designed for executing the method according to the invention.

The method for generating a favorites set containing multiple protocols can be in the form of computer code executed by the definition processor 33 when the electronically readable data medium 21 is loaded into the definition processor 33.

Figure 2:
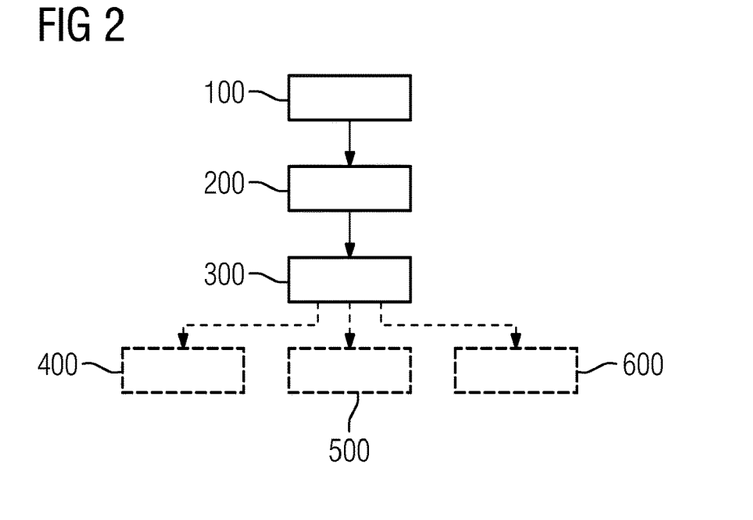
FIG. 2 is a flowchart of an embodiment of the method according to the invention.

FIG. 2 shows a flowchart of an embodiment of the method according to the invention for generating a favorites set containing a number of protocols, each protocol of the multiple protocols containing control parameters for controlling a medical imaging apparatus. The method shown is preferably executed only when the medical imaging device, i.e., the magnetic resonance apparatus is reconfigured.

The method starts with method step 100, the determination of a system parameter of the medical imaging device. Two or more system parameters may also be determined. A system parameter can be, for example, a software version of the medical imaging device and/or the presence and/or an embodiment of a specific component of the medical imaging apparatus.

In method step 200, at least one requirement is specified by a user of the medical imaging device, before in method step 300 the favorites set is defined, taking into account the at least one system parameter and the requirement, preferably by means of the definition processor 33. The requirement may be at least one of the following characteristics:
quality of the image data to be generated,
maximum and/or minimum duration of a protocol,
maximum and/or minimum duration for a set of protocols which are required for an examination of an examination object,
an examination area,
a clinical objective,
need for a contrast medium,
degree of automation,
possibility of custom post-processing of a protocol.

When defining the favorites set in method step 300, a subset is preferably selected from a core set, which core set includes multiple protocols for controlling the medical imaging device. The core set for this purpose is made available to the control computer 24, in particular to the definition processor 33.

If at least one requirement of the at least one requirement specified in method step 200 cannot be fulfilled when defining the favorites set in method step 300, then a protocol can optionally be proposed for selection to the user in method step 400, which protocol largely fulfills the at least one requirement.

In method step 500, the protocols of the favorites set can optionally be classified such that the protocols required for an examination of an examination object have an identical classification.

In method step 300, a favorites profile can optionally be taken into account when defining the favorites set. In method step 600, a user can optionally execute, based on the favorites set, a further customization of the favorites set of the medical imaging apparatus, and a self-learning algorithm can update the favorites profile based on the customized favorites set. Alternatively and/or additionally, the self-learning algorithm can update the favorites profile based on the favorites set defined in method step 300. The favorites profile can comprise two favorites sets, a first of the two favorites sets being assigned to a first magnetic resonance apparatus and a second of the two favorites sets being assigned to a second magnetic resonance apparatus.

The method steps 400, 500 and 600 can be executed optionally and independently of one another. At least two of the method steps 400, 500 and 600 can be executed at least in part simultaneously. At least two of the method steps 400, 500 and 600 can be executed consecutively.

Figure 3:
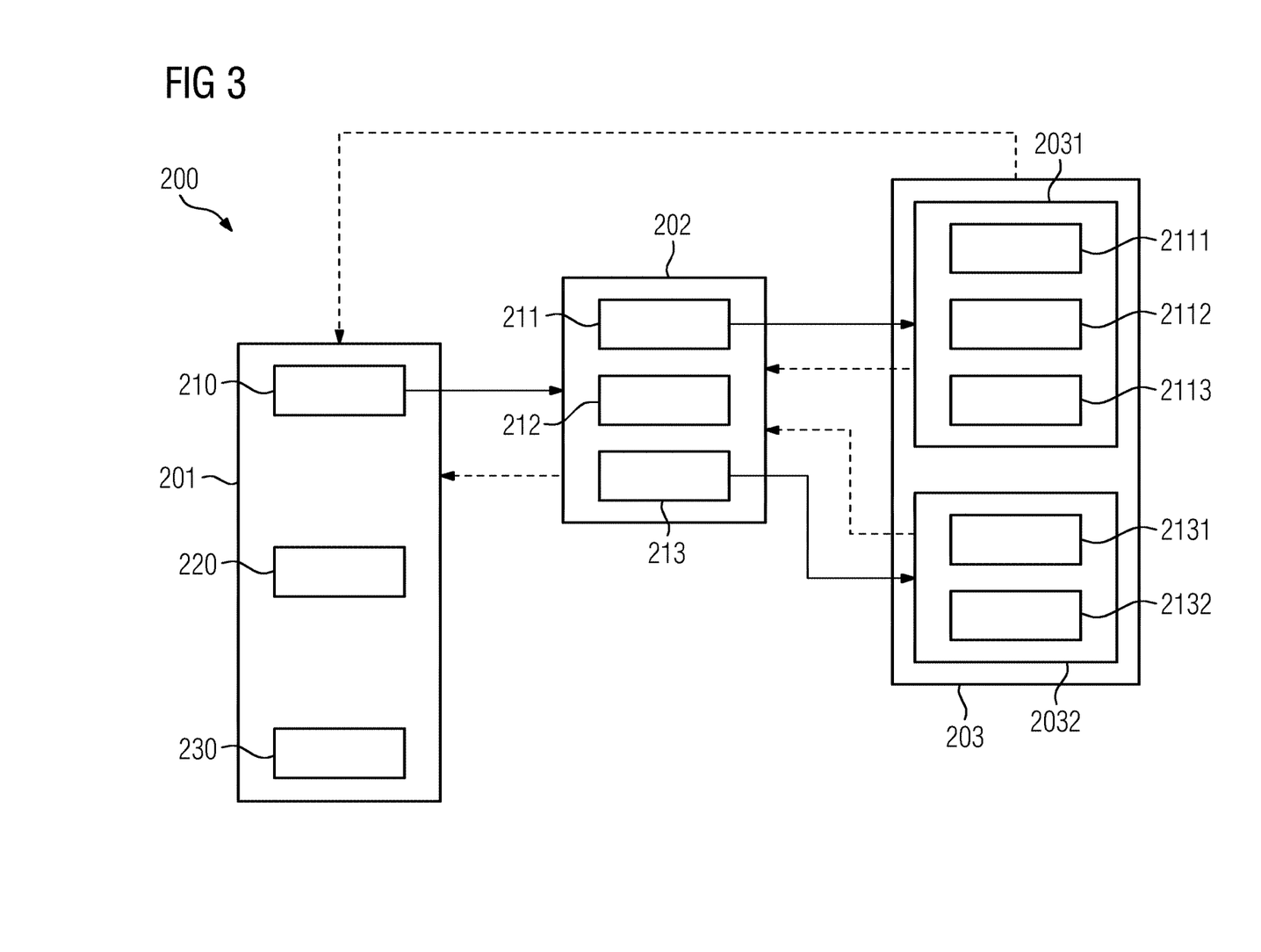
FIG. 3 illustrates a model for specification of a requirement by a user.

FIG. 3 shows a model for specification of a requirement by a user and gives a detailed example of an embodiment of method step 200. The requirement is specified via an input request to the user. Here, a number of requirements 201, 202, 203 may be specified iteratively, it being possible for a first 201 of the plurality of requirements 201, 202, 203 to be specified more precisely by a second 202 and optionally by a third 203 of the number of requirements 201, 202, 203. For example, the first requirement 201 can be an examination region, the second requirement 202 a clinical objective for this examination region and the third requirement 203 a desired maximum examination duration.

For example, the user may first be prompted to indicate a first requirement 201 by selecting one of the specified examination regions 210, 220, 230. If the user selects as a first requirement the examination region 210, for example the knee, then the user may next be prompted to enter as a second requirement 202 a clinical objective. Here, for example, the cartilage 212, the cruciate ligament 212 and the meniscus 213 may be listed for examination. Depending on the choice, the user may optionally be prompted to specify the examination further by indicating further requirements 203, 2031, 2032. Here, depending on the second requirement 202, for example, different requirements 2031, 2032 may be proposed to the user. Thus if the cartilage 212 is chosen as the second requirement 202 it can, for example, be selected whether the examination is to be executed with contrast medium 2121, what the maximum duration of the examination of the cartilage can be 2122 and whether the examination of the cartilage is to require a user interaction with the magnetic resonance apparatus 11 (degree of automation) 2123. If the meniscus 213 was selected as a second requirement 202, then for example the maximum duration of the examination 2131 and the use of a contrast medium 2132 could be selected as a third requirement 203, 2032.

After the second requirement 202 has been chosen and/or the third requirement 203 has been chosen, a new first requirement 201 and/or a new second requirement 202 can be selected. The interaction of the user is preferably controlled here such that all requirements relevant to the user are requested so that the user can customize the favorites set as far as possible.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for generating a favorites set of a plurality of protocols for controlling a medical imaging apparatus, said method comprising:
   in a computer, determining a system parameter of a medical imaging apparatus;
   making an entry into the computer that represents a requirement specified by a user of the medical imaging apparatus, the requirement identifying characteristics associated with a measurement to be performed by the medical imaging apparatus;
   in said computer, defining, dependent on the system parameter and the requirement specified by the user, a favorites set comprising a plurality of protocols, medical imaging apparatus such that the plurality of protocols included in the favorites set are compatible with the system parameter and attempt to fulfill the requirement specified by the user;
   presenting said favorites set to the user of the medical imaging apparatus at a display in communication with said computer; and
   if said requirement is not fulfilled when said favorites set is defined, (i) automatically generating, in said computer, an additional protocol that substantially fulfills said requirement, and (ii) presenting said additional protocol to the user via said display to allow the user to select the displayed alternate protocol.

2. A method as claimed in claim 1 comprising executing said method only upon a reconfiguration of said medical imaging apparatus.

3. A method as claimed in claim 1 comprising, after said favorites set is defined, selecting, in said computer, a subset of said favorites set from a core set comprising a plurality of protocols for operating said medical imaging apparatus.

4. A method as claimed in claim 1 comprising determining said system parameter as a parameter selected from the group consisting of a software version currently installed in said medical imaging apparatus, a presence of a predetermined component in said medical imaging apparatus, and a current embodiment of a predetermined component of said medical imaging apparatus.

5. A method as claimed in claim 1 comprising specifying said requirement from the group consisting of a quality of image data to be generated with said medical imaging apparatus, a maximum duration of a protocol, a minimum duration of a protocol, a maximum duration of set of protocols required for an examination of an examination subject, a minimum duration of a set of protocols required for an examination of an examination subject, an examination area of an examination subject, a clinical objective of an examination of an examination subject, a need for a contrast medium in an examination of an examination subject, a degree of automation of said medical imaging apparatus, and a requirement for customized post-processing of a protocol.

6. A method as claimed in claim 1 comprising, at said display, making a request for an input to said user and thereafter receiving said specification of said requirement by said user.

7. A method as claimed in claim 1 comprising specifying said requirement iteratively as a plurality of requirements, in which a first of said plurality of requirements is specified by a second of said plurality of requirements.

8. A method as claimed in claim 1 comprising, in said computer, classifying protocols in said favorites set so that protocols required for an examination of an examination object are classified in a same classification.

9. A method as claimed in claim 1 comprising providing said computer with a favorites profile and defining said favorites set using said favorites profile in an execution of a self-learning algorithm that updates the favorites profile based on the favorites set.

10. A method as claimed in claim 9 wherein said favorites profile comprises two favorites set, with a first of said two favorites sets being assigned to a first magnetic resonance apparatus and a second of said two favorites sets being assigned to a second magnetic resonance apparatus, as said medical imaging device.

11. A method as claimed in claim 1 comprising, in said computer, identifying a favorites profile and defining said favorites set dependent on said favorites profile and, via said display, allowing a user to execute a customization of said favorites set, and executing a self-learning algorithm in said computer to update the favorites profile based on the customized favorites set.

12. A method as claimed in claim 11 wherein said favorites profile comprises two favorites set, with a first of said two favorites sets being assigned to a first magnetic resonance apparatus and a second of said two favorites sets being assigned to a second magnetic resonance apparatus, as said medical imaging device.

13. A medical imaging apparatus comprising:
   a control computer configured to operate the medical imaging apparatus, said control computer having a display in communication therewith;
   said computer being configured to determine a system parameter of the medical imaging apparatus;
   said computer being configured to receive an entry made into the computer that represents a requirement specified by a user of the medical imaging apparatus, the requirement identifying characteristics associated with a measurement to be performed by the medical imaging apparatus;

said computer being configured to define, dependent on the system parameter and the requirement specified by the user, a favorites set comprising a plurality of protocols with each protocol in said plurality of protocols comprising control parameters for operating said medical imaging apparatus such that the plurality of protocols included in the favorites set are compatible with the system parameter and attempt to fulfill the requirement specified by the user;

if said requirement is not fulfilled when said favorites set is defined, automatically generating, in said computer, an additional protocol that substantially fulfills said requirement; and said computer being configured to (i) present said favorites set to the user of the medical imaging apparatus at said display in communication with said computer, and (ii) when said additional protocol is generated, present said additional protocol to the user via said display to allow the user to select the displayed alternate protocol.

14. A non-transitory, computer-readable data storage medium encoded with programming instructions, said storage medium being loaded into a computer system of a medical imaging apparatus and said programming instructions causing said computer system to:

determine a system parameter of a medical imaging apparatus;

receive an entry made into the computer system that represents a requirement specified by a user of the medical imaging apparatus, the requirement identifying characteristics associated with a measurement to be performed by the medical imaging apparatus;

define, dependent on the system parameter and the requirement specified by the user, a favorites set comprising a plurality of protocols, with each protocol in said plurality of protocols comprising control parameters for operating said medical imaging apparatus such that the plurality of protocols included in the favorites set are compatible with the system parameter and attempt to fulfill the requirement specified by the user;

present said favorites set to the user of the medical imaging apparatus at a display in communication with said computer system; and if said requirement is not fulfilled when said favorites set is defined, (i) automatically generating, in said computer, an additional protocol that substantially fulfills said requirement, and (ii) presenting said additional protocol to the user via said display to allow the user to select the displayed alternate protocol.

15. A method as claimed in claim 1, wherein the system parameter of the medical imaging apparatus is determined automatically via an algorithm and includes information associated with a component of the medical imaging apparatus.

16. The method as claimed in claim 15, wherein the control parameters for operating the medical imaging apparatus included in the plurality of protocols are extracted from the system parameter.

17. A method as claimed in claim 2, wherein reconfiguration of the medical imaging apparatus includes updating the system parameter, and wherein executing the method upon the reconfiguration of the medical imaging apparatus includes updating the favorites set to utilize the updated system parameter of the medical imaging apparatus.

18. A method as claimed in claim 1, wherein the requirement specified by the user is from among a number of requirements, with each requirement identifying characteristics associated with a respective measurement to be performed by the medical imaging apparatus, and wherein the plurality of protocols included in the favorites set are compatible with the system parameter and attempt to fulfill each of the number of requirements specified by the user.

19. A method as claimed in claim 18, wherein the number of requirements specified by the user include a prioritization, and wherein the favorites set are defined by weighting the prioritizations specified by the user.

* * * * *